(12) United States Patent
Valencia

(10) Patent No.: US 8,883,229 B2
(45) Date of Patent: Nov. 11, 2014

(54) PESTICIDAL COMPOSITIONS AND RELATED METHODS

(76) Inventor: José Luis Miranda Valencia, Celaya (MX)

( * ) Notice: Subject to any disclaimer, the term of this patent is extended or adjusted under 35 U.S.C. 154(b) by 103 days.

(21) Appl. No.: 13/055,513

(22) PCT Filed: Oct. 5, 2009

(86) PCT No.: PCT/MX2009/000103
§ 371 (c)(1),
(2), (4) Date: Oct. 26, 2011

(87) PCT Pub. No.: WO2010/098649
PCT Pub. Date: Sep. 2, 2010

(65) Prior Publication Data
US 2012/0040032 A1    Feb. 16, 2012

(30) Foreign Application Priority Data

Feb. 24, 2009 (MX) .................. MX/a/2009/002081

(51) Int. Cl.
*A61K 36/8962* (2006.01)
*A01N 65/42* (2009.01)
*A01N 65/00* (2009.01)

(52) U.S. Cl.
CPC .............. *A01N 65/00* (2013.01); *A01N 65/42* (2013.01)
USPC .......................................... 424/754; 424/725

(58) Field of Classification Search
USPC ........................................................ 424/754
IPC .................................................. A61K 36/8962
See application file for complete search history.

(56) References Cited

U.S. PATENT DOCUMENTS

| 5,174,804 A | 12/1992 | Rehberg et al. |
| 6,511,674 B1 | 1/2003 | Arand et al. |
| 6,548,285 B1 | 4/2003 | Swinkels et al. |
| 2004/0063582 A1 | 4/2004 | Johnson |
| 2004/0118037 A1* | 6/2004 | Catalano .................. 47/1.01 R |
| 2010/0003341 A1* | 1/2010 | Besendorfer ................ 424/616 |

FOREIGN PATENT DOCUMENTS

| AU | 2019588 | 2/1998 |
| KR | 100869349 | 11/2008 |
| WO | WO 2007/041885 | 4/2007 |
| WO | WO 2007/041886 | 4/2007 |
| WO | WO 2007/046680 | 4/2007 |
| WO | WO 2007/144694 | 12/2007 |
| WO | WO2007144694 | 12/2007 |

OTHER PUBLICATIONS

Jose Luis Miranda Valencia; PCT/MX2009/000103; International Search Report dated Sep. 2, 2010.

* cited by examiner

*Primary Examiner* — Chris R Tate
(74) *Attorney, Agent, or Firm* — Thorpe North & Western LLP

(57) ABSTRACT

The present invention relates to a botanical repellent composition intended for pest insect control. In some embodiments, the composition may contain about 75% to about 92% garlic extract (*Allium sativum*) and about 8% to about 25% humic acids and diluents.

6 Claims, No Drawings

US 8,883,229 B2

PESTICIDAL COMPOSITIONS AND RELATED METHODS

FIELD OF THE INVENTION

The present invention relates to botanical repellent compositions which can be used for pest control. Accordingly, the present invention relates to the fields of chemistry and biology.

BACKGROUND OF THE INVENTION

The synthetic products used for controlling plant diseases and pests have had an important role on the increasing of the agriculture production. However the constant and indiscriminate use of these substances, have not just caused illness (Waterhouse, 1996) and death poisoning in short and long term, it also has affected the environment, accumulating in different steps of the food chain, in the soil and water. They are responsible of the resistance created by insects to insecticides, without having to diminish importance to the destruction parasites, natural predators and pollinators, among others ecosystem inhabitants that have seen disturbed their life cycle because of these products. Humans depend directly on plants whether they be vegetables, crops, cereals or the process products of them. Every year a third part of the food production is destroyed by pests on crops or warehouses, because of this it is necessary to study new ways for controlling these plagues. Plants, as a whole, produce more than 100,000 substances of low molecular weight also known as secondary metabolites. These are not normally essentials for the basic metabolic process of the plants. Among them we can find terpenes, lignanes, alkaloids, sugars, steroids, fatty acids, etc. This chemical diversity is consequence of the evolve process made by different species to improve their defenses against diseases or animal and insects predation. In the present we know that the secondary metabolites have an important role on the plants defensive mechanism. Therefore in the last years it is returning the use of plants as source of pesticides that are more secure to environment and human health. Pesticides can be classified according to the type of organism they are active: fungicides, herbicides, insecticides, nematicides, molluscicides, rodenticides. Undoubtedly natural insecticides made with plants extracts are an interesting alternative for controlling insects, besides a very few plants have been tested compared to what the natural source on the planet has to offer. The investigation perspectives in the near future are huge due to this.

Beginning from the need of finding new natural alternatives for controlling pest insects and replacing the old synthetic pesticides, botanic insecticides have shown up; offering environment security and agronomic efficiency. Many plants are capable of synthesize secondary metabolites with biological properties against pests insects. The selection of plants containing secondary metabolites with insecticide activity has to be: easy crop management, potent active ingredient, chemical stability, optimal production. Such is the case for the Patent 176535 that consists on elaborating a product derivate from piridazone and compositions for controlling and preventing pest insects.

As we know most of the chemical pesticides are expensive and toxic for humans, animals and the environment, and persist a lot longer after they have been applied.

Garlic, for example, has been used as an animals and insects repellent, and its antimicrobial properties have been studied widely. However it success as an agrochemical pesticide has been limited due to its low effectiveness.

One of the problems of using natural pesticides such as essential oils is that they are highly volatile and the time of action is for a very few moments.

The routes for improving this effect have been described on the document U.S. Pat. No. 6,548,285, that describes a combination of the citric oil and a synergist compound (sodium lauryl sulfate) and essential oils, such as garlic, as a synergic insecticide.

The document U.S. Pat. No. 6,231,865 describes a synergic mixture of oil and garlic extract and cinnamon and cotton oil as natural insecticide for inhibiting the growth of insects.

The garlic extract is obtained by combining and mixing the garlic cloves with water, oil or organic solvents.

The document U.S. Pat. No. 6,511,674 describes one of the reasons because of why the garlic has low efficiency; this reason is that the extract has a low quantity of garlic; besides describes how to use a solution of the garlic extract with a concentration quantifiable more than a 10% in weight of the garlic extract and a second compound from an agricultural treatment agent like a pesticide, miticide, fungicide, antibiotic, herbicide, defoliant, nutrient, adjuvant and water. This composition just presents a concentration higher than 10%, in contrast to the composition of the invention here presented that has a concentration of garlic extract of 87% which makes it highly effective, and 13% of humic acids and water, for introducing into the vascular system of the plant and enhance its 4 action mechanisms for fighting plague insects. Besides it does not present any component from an agricultural treatment agent of a pesticide.

The document WO 2007/046680 (MX/a/2007/015628) describes an insecticide organic mixture for controlling *Aedes aegypti* (malaria mosquito) and some other plague insects. The insecticide comprising an extract of *Quillaja saporia*, which function is to destroy the insect's chitin, an extract of *Chrysantemum cenerariaefolium* (piretrines), which function is to attack the nervous system of the insect, an extract of azadirachtin which function is to interrupt the metamorphosis, inhibit the feeding and prevent them to approach, and an aqueous extract of garlic (*allium* spp.) which only function is as an insect repellent.

The document WO 2007/041886 (MX/a/2008/004311) describes fungicide preparation for controlling plagues and fungus in seeds and plants, which is composed of i) a fungicide compound of a) an allyl sulfure (garlic oil) and b) an alkyl or alkenyl benzene replaced in a proportion 1:19 (eugenol and thymol) and as an option ii) one or more additional constituents, oils selected from garlic, clove and thymus, in which a) is provided from garlic oil and b) is provided from clove an thymus oil.

The document WO 20074/041885 (MX/a/2008/004312) describes a pesticide preparation for nematodes, composed by a mixture of garlic and allyl azothiocianates from mustard oil in a proportion 90:10. It is solid for facilitate its use and application on soil.

The document WO 2007/144694 (MX/a/2008/004819) describes a natural pesticide based on the combination of garlic powder and mustard oil in a proportion 85:15 for inhibiting the growth of bacteria, fungus and eradicating insect pests.

All the compositions mentioned on the last documents are different to the botanical repellent composition containing *Allium sativum* and humics acids and intended for pest insect control, in which a garlic aqueous extract is used as active ingredient as repellent, humic acids are used as bioprotector agents and coadjuvants for the entry of garlic extract into the vascular system of the plant, because there is no mention of a composition based in humic acids for increasing amazingly the repellent effect as indicated, therefore is considered not to affect the novelty, nor the inventive activity on the present invention, due to achieve a surprising repellent effect, improved by its high garlic extract concentration, that is not achieved by the known repellents based in garlic as an active ingredient.

DESCRIPTION OF THE INVENTION EMBODIMENTS

The present invention relates to a botanical repellent composition containing *allium sativum* and humics acids and intended for pest insect control, in which an aqueous extract of garlic is used as active ingredient, and humic acids and water as diluents, it has a surprising repellent effect compared to others already known.

The garlic extract in the composition makes it highly effective repelling insects and humic acids and the water are the access via to the vascular system of the plant and enhance the 4 action mechanism for the combat of the pest insect.

The humic acids also work as bioprotector agent coadjuvant for the entry of garlic extract into the vascular system of the plant which enhance it repellent effect.

The composition proposes provide a botanic repellent for pests insect based on an aqueous garlic extract. It is recommended for using in Integrative Crop Management programs or Organic Agricultural production. It has a broad spectrum of action against virus vectors like whitefly, increasing the masking effect of pheromones and crops odors. It can disturb the reproduction and feeding habits. In the crop protection it works trough 4 basic effects that affects directly on the behavior and physiology of insects:

REPELLENT EFFECT: by means of systemic action, the garlic extract is absorbed by the plant trough the vascular system; altering the enzymatic activity, making changes in the transpiration and changing the composition of the intracellular juices and the sap.

MASKING EFFECT: it masks the effect of the pheromones produced by the insects reducing the reproduction, which means an interruption on their life cycle.

ANTI-FEEDING EFFECT: when the insects make contact with the garlic, it modifies their feed habits, making the crops less desirable and because of that hard to digest.

HYPER EXCITING EFFECT OF THE NERVOUS SYSTEM: this effect is caused by substances from garlic extracts known as thiosulphates. These substances make the insects to be altered and cause confusion.

The present invention relates to a botanical repellent composition containing extract of garlic (*allium sativum*), humics acids and diluents intended for pest insect control, in which the humic acids creating a bigger repellent effect.

The botanical repellent composition for intended for pest insect control comprising 75 to 92% garlic extract (*Allium sativum*), 8 to 25% humic acids and diluents.

The diluent can be water, but it also can be any other.

In a preference modality the botanic repellent composition for intended for pest insect control comprising:

| Component | Concentration |
|---|---|
| Aqueous garlic extract (*Allium sativum*) | 87.00% |
| Humic acids and diluents | 13.00% |

Surprisingly these percentages provide controls effectiveness of more than 70% for the adults, more than 60% for the pupae and more than 60% for the eggs of whitefly (*Bemicia tabaci*) in pumpkins (*Cucurbita pepo*).

The percentages, in weight, are based on the total weight of the botanic repellent; in which the organic matter is obtained from the garlic extract (*Allium sativum*) this extract is obtained macerating with an alcoholic solvent, without damaging the active ingredients. The humic acids provides a bioprotector effect that contributes surprisingly to the repellent effect of this composition, they increase the membranes permeability making easier the systemic action of the garlic extract. They stimulate plant biochemistry contributing with the change of the intracellular juices, when these juices are expelled trough transpiration they create the repellent effect. They increase the nutrients absorption and promote growth in the plant giving to them more resistance. Besides the humic acids provides the characteristic color of the product and they can help it to last longer.

These concentrations of the components have a surprising and repellent effect. The garlic is an excellent insect and animal repellent, as such, its extract is used for blocking coloeoptera and homoptera pests.

The repellent effect is associated to the systemic action of the garlic extract; it is incorporated to the plants vascular system modifying its scent and, for that, it modifies the natural behavior of its natural pests.

The Garlic Plant

The garlic bulb comes from center and south Asia, from where it spreads to the Mediterranean area, and then Europeans were responsible of spreading it to the rest of the world. The garlic plant has tiny whitish flowers, with six petals arranged in umbrella.

The fruit is a capsule with black kidney seeds. The garlic plant is commonly cultivated from the bulb; the bulb has intense and characteristic odor and flavor; it is covered with a papyrus wrapping and it is conformed of several pieces that are easy to separate known as garlic cloves. It has a substance known as alliin, when it is fermented it transforms into allyl disulfurs; which are the responsible of the characteristic odor. The reproduction of the garlic plants can be sexual or asexual.

Root: it has numerous, fine, simple and lock form roots; they are not able to reach long depths.

Bulbs: The garlic cloves are joined in their base by a thin layer, forming what is commonly known as "garlic head". Each garlic clove is wrapped by a white; sometimes red; transparent and thin membrane, similar to the one that covers the bulb.

Leaves: they are long and come from the root; they do not have any nerve, apparently.

Stem: It comes in the middle between the leaves. It is hollow, it seems like a roll, it is hairless and, it grows from 40 cm to more than 55 cm; it ends where the flowers start to grow.

Flowers: they are contained on a membranous spathe that opens longitudinally at the flowering time. They group in a form that seems like an umbrella.

Taxonomic Classification:
Family: Alliliaceae
Subfamily: Allioideae
Name: *Allium sativum* L.
Garlic Geographic Location Mexico through the years is been one of the biggest garlic producers in the whole world, placing itself in the top ten for the production volume. In Mexico the states of Guanajuato, Aguascalientes, Zacatecas, Puebla, Sonora, Queretaro and San Luis Potosi can reach over the 94% of the garlic total production.

TABLE 2

Total garlic surface on 2006, fall winter cycle, irrigate.

| State | Surface Seeded (Ha) | Surface Harvested (Ha) | Production Volume (ton) | Yield (ton/Ha) |
|---|---|---|---|---|
| Aguascalientes | 262 | 262 | 2,911 | 11.111 |
| Guanajuato | 1,129.90 | 1,129.90 | 9,104.70 | 8.058 |
| Puebla | 318 | 318 | 1,703 | 5.355 |
| Queretaro | 64.00 | 64 | 492 | 7.688 |
| San Luis Potosi | 39 | 39 | 337 | 8.641 |
| Zacatecas | 1,364.00 | 1,364 | 14,179.10 | 10.395 |

Source: SAGARPA (2006)

Garlic Chemical Composition

The biochemical composition is represented by condensed fructosane type, glucides and glutamyl dipeptides with sulfur radicals; in the last group we can find the one that is formed with glutamic acid and allycysteine sulfoxyde, better known as alliin. This compound is the one that gives the characteristic flavor and the antibiotic properties to raw garlic. When clove tissues are broken, they suffer a biochemical transformation by means of the alliinase enzyme; during this process the compound decompose into two molecules of piruvic acid, one molecule of allicine and two molecules of ammoniac. These products have an interesting miticide and insecticide action although they lose their antibiotic properties. The entire bulb has a large quantity of alpha-glutamyl-cysteines. These reserve compounds are hydrolyzed and oxidized to create the alliine; this last compound accumulates during the garlic storage. If the garlic is damaged the enzyme alliinase is released, this enzyme acts quickly lysing the cytosolic cysteine sulfoxydes (alline) and form thiosulphinates; these are cytotoxic aromatic compounds. These thiosulphinates that are about 70-80% of alliicine decompose quickly into other compounds like diallyl polysulfide (DAD, DADS, and DAT), ditiins and ajoenes, at the same time; a part of the alpha-glutamyl-cysteines is converted into S-alycysteine (SAC) by means of another non known metabolic route. (Amagase, 2001)

Besides these compounds, garlic contains: glycosides, lectins, prostaglandins, fructan, pectin, adenosine, thiamin, riboflavin, pyridoxine, vitamin C, vitamin E, biotin, nicotinic acid, fatty acids, glycolipids, phospholipids, antocianins, flavonoids, phenols and essential amino acids. Several of these substances act in a synergic way to increase the garlic intrinsic properties.

TABLE 1

Composition in 100 grams of food product

|  | (1) | (2) | (3) | (4) | Units |
|---|---|---|---|---|---|
| Waste | — | 20 | — | — | g |
| Water | 61 | 61 | 63 | — | g |
| Proteins | 4 | 6.4 | 6.7 | 3.33 | g |
| Lipids or fats | 0.5 | 0.5 | 0.1-0.2 | 0.167 | g |
| Glucides or carbohydrate | 20 | 2.9 | 28 | 16.67 | g |
| Cellulose or fiber | — | — | 1 | 0.83 | g |
| Vitamin B or Thiamin | 0.20 | 0.20 | 0.18-0.21 | — | mg |
| Vitamin $B_2$ or Riboflavin | 0.11 | 0.11 | 0.08 | — | mg |
| Vitamin C | 9-18 | 15 | 9-18 | — | mg |
| Niacin or Nicotinic acid | 0.7 | 0.7 | 0.6 | — | mg |
| Calcium | 10-24 | 24 | — | — | mg |
| Iron | 1.7-2.3 | 1.7 | 2.3 | — | mg |
| Magnesium | — | 32 | — | — | mg |
| Phosphorus | 40-195 | 195 | — | — | mg |
| Potassium | 540 | — | — | — | mg |
| Selenium | — | — | — | 9 | ppm |
| Energetic content | 98-139 | 100-139 | — | — | cal |

(1) Fersini, 1976 and Gorini 1977.
(2) Yamaguchi, 1983.
(3) Japon Quintero, 1984.
(4) Fulders S., Blaewood J. adapted according to the authors an average clove weights 6 grams.

Chemical Composition of the Garlic Extract

The garlic and its extracts are considered as GRAS (Generally Recognized as Safe) by the Agency for the Protection of the Environment (EPA, 1992). The garlic compounds can be classified in two groups:

1.—Lipophilics: We can find them in the garlic essential oil. They are derivative from the alliicine, mainly polyalliil disulfide, ajoene and vinyltidins. The essential oil has certain toxicity, because of this it can act as bactericide, acaricide, antihelminthics, fungicide, insecticide, etc. It has cholesterol and lipids reductive properties.

2.—Hydrophilics: We can find them on the garlic aqueous extract, in the begging they are a mixture of alliine and alliicine, this mixture during time degrades in S-allyl-L-cysteine (SAC), S-allyl-L-mercaptcysteine (SAMC), saponins and small quantities of lipophilic compounds. It is not cytotoxic, and it results to be an insect repellent and also has some cholesterol reductive properties.

Extraction of the Garlic Juice to be Applied in the Botanic Repellent

The gathering process of a garlic fluid extract is performed through a macerating method, which consists in put the garlic bulbs through a process of cleaning, grist, mixing and compressing with a single alcoholic solvent, without harming the active ingredients, it takes places as the follow description:

a) The first step consists in bulbs selection, they should be as bigger and heavy as possible, when we exclude the lighters we are selecting the healthiest garlic since the unhealthy bulbs usually tends to lose weight, we should eliminate bulbs with malformations like bulge, smashed or opened bulbs, and finally should be excluded the bulbs disease symptoms, like, rot, greenish dust, yellowish dust or grease spots.

b) The next step consists on cleaning the material, to eliminate dust and other residues each garlic clove is washed with detergent and water.

c) After cleaning the material, it is rinsed with plenty of water to eliminate the detergent residues. Once the garlic cloves are clean they are passed through a mill or an industrial blender, the garlic should be milled as fine as possible in order to break as much garlic cells as possible and enable the alliinase to have contact with the alliin. In this step for each kilogram of garlic 840 mL of water and 1 g of salt are added.

d) The grist garlic is introduced into a stainless steel container and is covered with ethanol (1.5 L/1 kg of garlic). This mixture is shaked 20 minutes every 3 hours during a rest time of 25 days.

e) When the 25 days have passed the mixture is poured into 20 liters containers.

f) The mixture is filtered through a #110 mesh. The objective of this step is to separate at a moderate speed the substrate from the extract.

g) The resultant liquid is filtered again through a #325 mesh.

h) The garlic extract is added to the repellent diluting this mixture with water.

i) The repellent is putted in 19 L bottles for it to be sale and distributed.

The type and concentration of the garlic extracted compounds depend on the maturity of the plant (Lancaster, et al., 1984) agricultural and production practices (Mazza, 1998) location of the crop (Freeman, 1975) and processing conditions (Malkeja, 1990). The gathering of the scent and garlic extracts, the dehydrated, canned and freezing leads to make products with different physical and chemistry characteristics and biological properties (f.e. the alliicin has a half-life that can be from hours to days it depends on the solvent used during the extraction or the medium pH since the alliinase; enzyme responsible of the formation of alliicin; at low pH has no activity). The storage seems to affect on the increasing of the sulfur compounds, probably because of the gradual formation of S-alk(en)yl-L-ciyten sulfoxydes from g-glutamic precursors (Freeman, 1976). On the other side, the garlic sulfur compounds unchain a unique set of chemicals reactions, these are the ones that generate a lot of their metabolic effects.

Most of the sulfur components are no present on the cells. When garlic is smashed or cut, several of its sulfur components are released from the inside of the plant cells; then there is an interaction of each other of the components making a chain reaction that generates a large set of components. Thus for example, when the cell breaks there is a reaction between the enzyme alliinase and its volatile precursors (S-alkenyl-cystein sulfoxyde and sulfonic acid) resulting on the formation of several thiosulfinates and some other compounds related with the sulfonic acid (reaction scheme 1). The products generated from the decomposition of the sulfinates such as alliicin (diallyl thiosulfinate) can happen through different metabolic routes. One of these routes combines three alliicin molecules and produces two ajoene molecules. Through another non enzymatic reactions the thiosulfinate are transformed into other sulfur compounds such as mono, di, tri and tetra sulfurs, thiols, thiophenes, and sulfurous oxide.

Alliicin can be produced when garlic is extracted with water and ethanol at room temperature, this compound is the responsible of the garlic odor. Alliin can be produced with a softer extraction using absolute ethanol at temperatures bellow 0° C. (Bloc, 1985) (scheme reaction 1). The alliin can be decomposed, in presence of alliinase, into 2-propensulfonic acid which dimerize in alliicin (Block, 1985), it is a substance that has different kind of functions one of these functions is insect repellency. The garlic compounds show different qualities in its bio-availability, and effects over other living organisms.

Scheme reaction 1

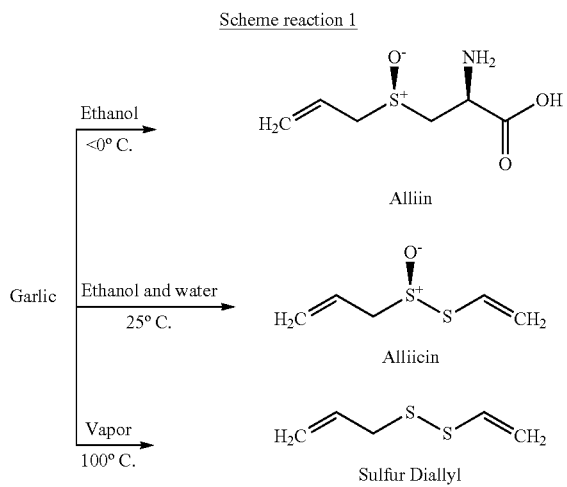

Alliin

Alliicin

Sulfur Diallyl

Effects caused by the processing of garlic during the formation of different garlic active compounds.

The research for methods for natural crops protection is still active even though the mark has a lot of products to offer. Nature gives us many crop protection ways that deserve our attention. These were created by the species in their fight to survive. The natural crops protection minimizes the risk of species to create resistance, has fewer consequences to natural enemies of the plagues, and makes less probable the appearance of secondary pests, they have fewer toxic effects on the human being, and make no harm to the environment.

Alternatively, natural products that come from plants act inhibiting, repelling, or eliminating distinct plague insects (sucking insects, chewing insects, flying insects, etc.) and also stimulating the crops to make them stronger and so protect themselves against distinct pests.

Below are some examples with that explain the invention and no to limit it, any variation of the technique can be considered part of this.

Example 1

For producing 1000 liters of botanic repellent composition, 850 liters of water are mixed with 100 liters of garlic extract and 50 liters of humic acids, the mixture is done according to the next procedure; raw material is received and storage in containers, then its composition is reviewed and the formula is adjusted, the water is added to the mixing tank, then the garlic extract and finally the humic acids, these components are mixed for 30 minutes after the time is elapsed a sample is taken to the lab for it to be analyzed and authorized. As last step the product is bottled in its corresponding presentation.

Example 2

A botanical repellent composition for intended for pest insect control comprising 75% to 92% garlic extract (*Allium sativum*), 25% to 8% humic acids and diluents, and it is applied in spray.

The botanical repellent composition the garlic attacks aphids, whitefly, armyworm, grasshoppers, weevil, white grubs, cabbage worm, Mexican bean beetle, false apple moth, Colorado potato beetle, red spider and nematodes.

The application procedure is as follow:

1) Fill the application tank with ¾ of its total capacity; add the botanic repellent composition that from now on we are going to call "AJICK", of 2 to 3 L/Ha, fill the container total capacity and mix it constantly.

2) It can be applied by manual spray, motorized spray or with an airplane.

3) The water volumes per hectare for aerial application can be from 25 to 30 L and for ground application can be from 100 to 200 L.

The botanic repellent composition may be applied in many ways, is recommended start the application early on the day or in the afternoon during the sunset, it is not recommendable to be applied during intense heat and solar radiation moments. For the mixture are suggested use plastic recipients or other non ionizing material, and also adjust the water pH to 6.0, this product promotes ecologic equilibrium on the crop surrounding environment, it also reduces or eliminates the physiological stress caused because of the phytotoxicity. Every dose should be applied with sufficient water to ensure a good coverage, depending on whether it is applied with band spraying or total spraying.

In biological efficacy trials the product "AJICK" (aqueous garlic extract) has shown the best efficacy on adults, nymphs and eggs of whiteflies (*Bemisia tabaci*) in pumpkins (*Cucurbita pepo*) crop with a dose of 32.0 L/Ha, an average efficacy of 60.90% for adults, 58.32% for nymphs, and 62.19% for eggs, because of these results it is widely recommended as a part of an integrated crop management program, using the kindness of the product by preserving the beneficial fauna and the low pollution it generates.

It is recorded until the present date that the best known method for the solicitant to carry out the present invention, Is the one that is described in the present document.

The invention claimed is:

1. A liquid botanical repellent composition for pest insect control comprising:
   from about 75 wt % to about 92 wt % of an aqueous-alcoholic extract (*Allium sativum*); and
   from about 8 wt % to about 25 wt % of a humic acid and diluent mixture.

2. The composition of claim 1, wherein the diluent is water.

3. The composition of claim 1, wherein the composition comprises 87 wt % of the aqueous-alcoholic garlic extract and 13 wt % of the humic acid and diluent mixture.

4. A botanical repellent composition for pest insect control comprising: 100 L of an aqueous-alcoholic garlic extract, 50 L of humic acid, and 850 L of water for each 1000 L of composition.

5. A method of repelling pests from plants comprising:
   providing a composition as recited in claim 1; and
   administering an effective amount of the composition to a plant, wherein the composition provides control effectiveness of more than 70% for the adult pests, more than 60% for the pests in a pupae stage and more than 60% for the eggs of whiteflies (*Bemicia tabaci*) in pumpkins (*Cucurbita pepo*).

6. A method of repelling pests from plants comprising:
   providing a composition as recited in claim 4; and
   administering an effective amount of the composition to a plant, wherein the composition provides control effectiveness of more than 70% for the adult pests, more than 60% for the pests in a pupae stage and more than 60% for the eggs of whiteflies (*Bemicia tabaci*) in pumpkins (*Cucurbita pepo*).

* * * * *